United States Patent
Shabat

(10) Patent No.: US 9,028,252 B1
(45) Date of Patent: May 12, 2015

(54) DEVICE, SYSTEM AND METHOD FOR IN-SITU DRILL GUIDE SLEEVE ORIENTATION

(71) Applicant: Roni Shabat, Kfar Yehezkel (IL)

(72) Inventor: Roni Shabat, Kfar Yehezkel (IL)

(73) Assignee: Navident Medical Device Ltd., Natzrat-Elit (IL)

( * ) Notice: Subject to any disclaimer, the term of this patent is extended or adjusted under 35 U.S.C. 154(b) by 0 days.

(21) Appl. No.: 13/975,385

(22) Filed: Aug. 26, 2013

Related U.S. Application Data

(60) Provisional application No. 61/693,345, filed on Aug. 27, 2012.

(51) Int. Cl.
| | |
|---|---|
| *A61C 3/04* | (2006.01) |
| *A61C 1/08* | (2006.01) |
| *A61C 13/15* | (2006.01) |
| *A61C 8/00* | (2006.01) |

(52) U.S. Cl.
CPC ............... *A61C 1/084* (2013.01); *A61C 19/003* (2013.01); *A61C 8/0089* (2013.01)

(58) Field of Classification Search
CPC ........ A61C 1/082; A61C 1/084; A61C 1/085; A61B 17/176; A61B 17/17

USPC .......................... 433/75–76, 172–176; 606/96
See application file for complete search history.

(56) References Cited

U.S. PATENT DOCUMENTS

| | | | | |
|---|---|---|---|---|
| 8,388,342 | B2 * | 3/2013 | De Clerck | 433/174 |
| 2004/0219479 | A1 * | 11/2004 | Malin et al. | 433/75 |
| 2005/0282106 | A1 * | 12/2005 | Sussman et al. | 433/76 |
| 2006/0093988 | A1 * | 5/2006 | Swaelens et al. | 433/76 |
| 2007/0281270 | A1 * | 12/2007 | Brajnovic | 433/72 |
| 2009/0004625 | A1 * | 1/2009 | Esposti et al. | 433/165 |
| 2010/0255441 | A1 * | 10/2010 | Taormina | 433/75 |

* cited by examiner

*Primary Examiner* — Yogesh Patel
(74) *Attorney, Agent, or Firm* — The Law Office of Joseph L. Felber

(57) ABSTRACT

The present invention relates to a device, system and method for producing a dental implant drill guide and in particular to such a device system and method for positioning a sleeve within a drill guide to determine the drill path for positioning a dental implant at an implantation site over the entire edentulous site where the sleeve may be fixed in its position and orientation anywhere about the edentulous area having full range of motion thereabout, while the sleeve orientation may be fixed by introduction of a curing agent.

37 Claims, 8 Drawing Sheets

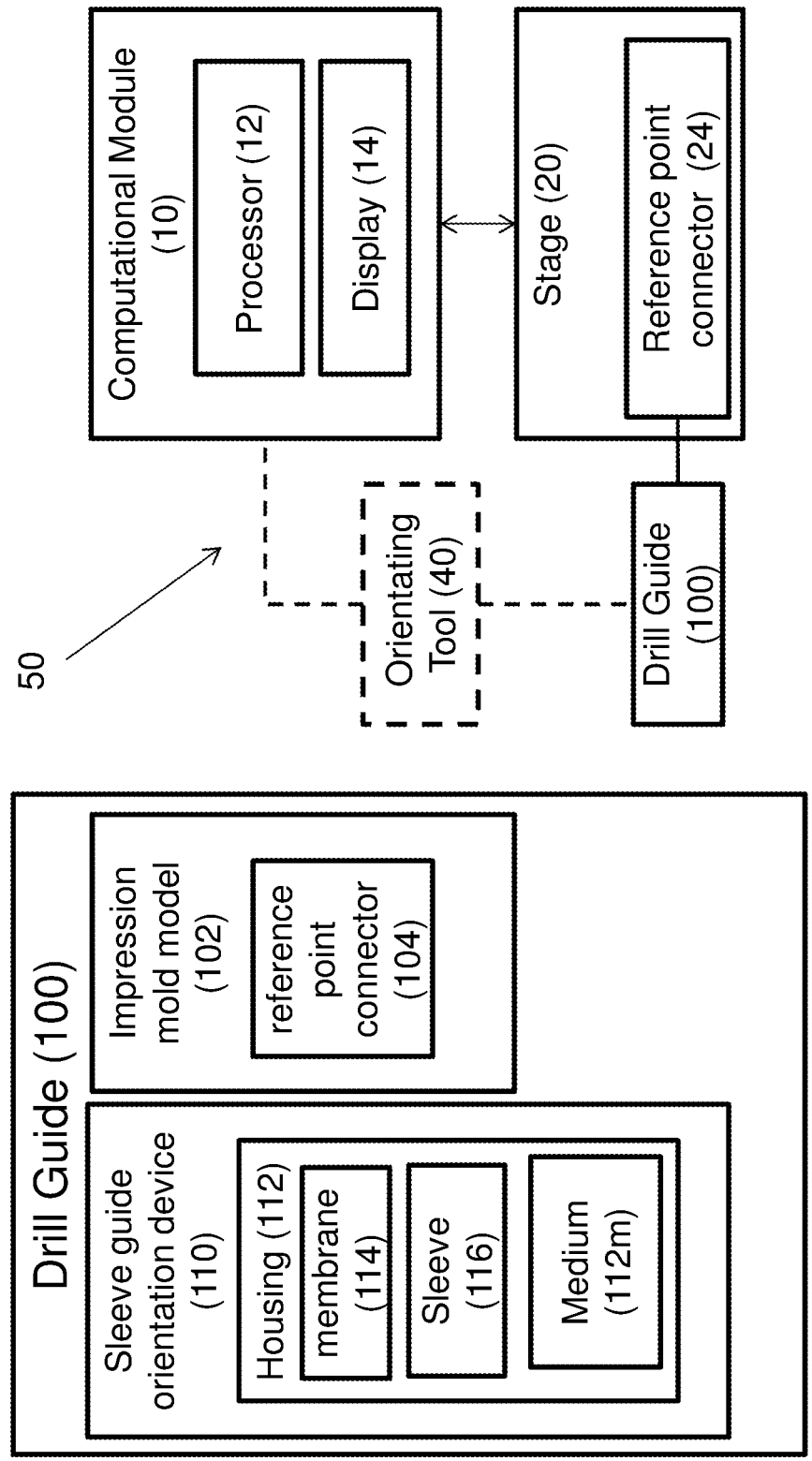

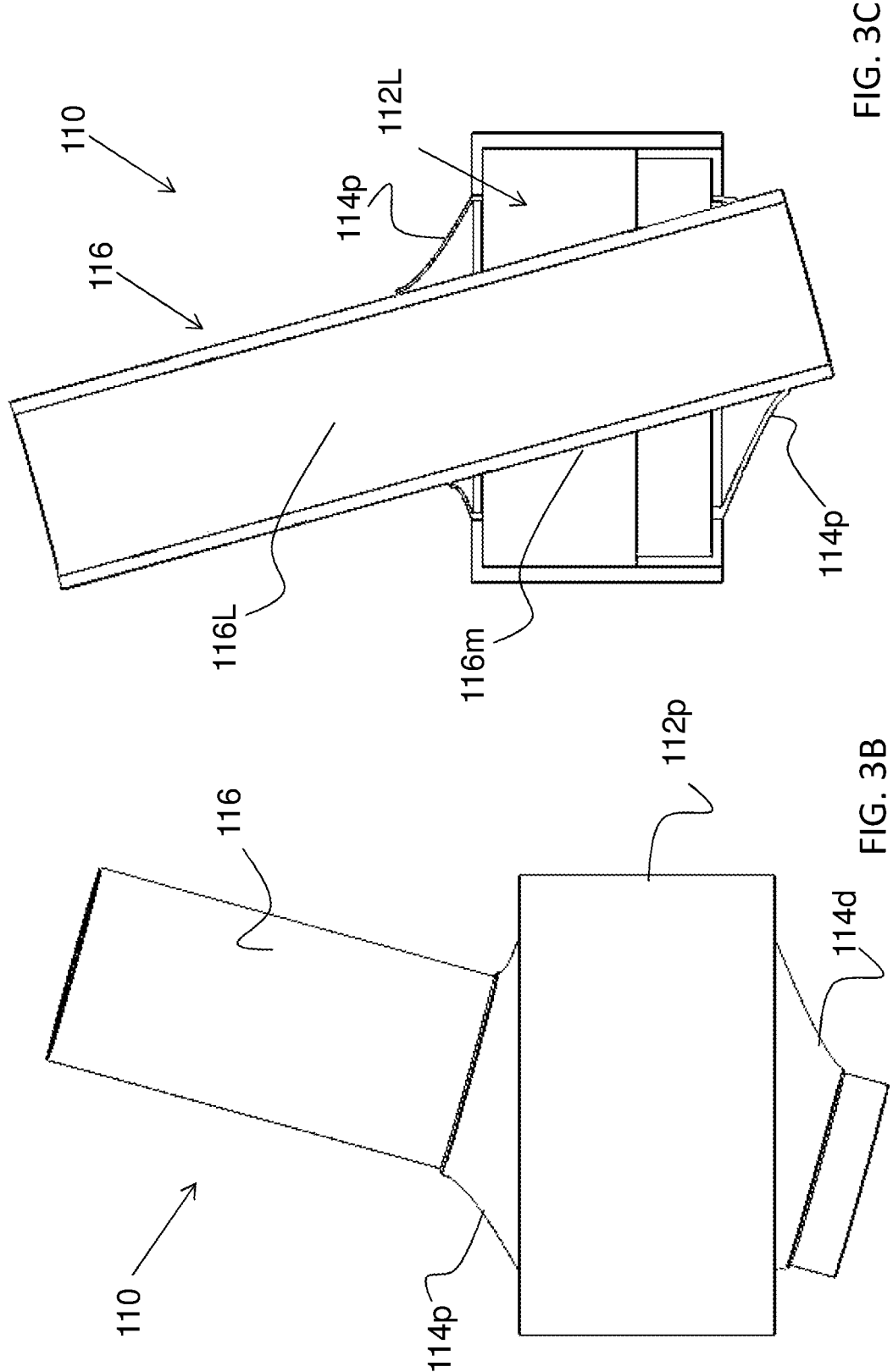

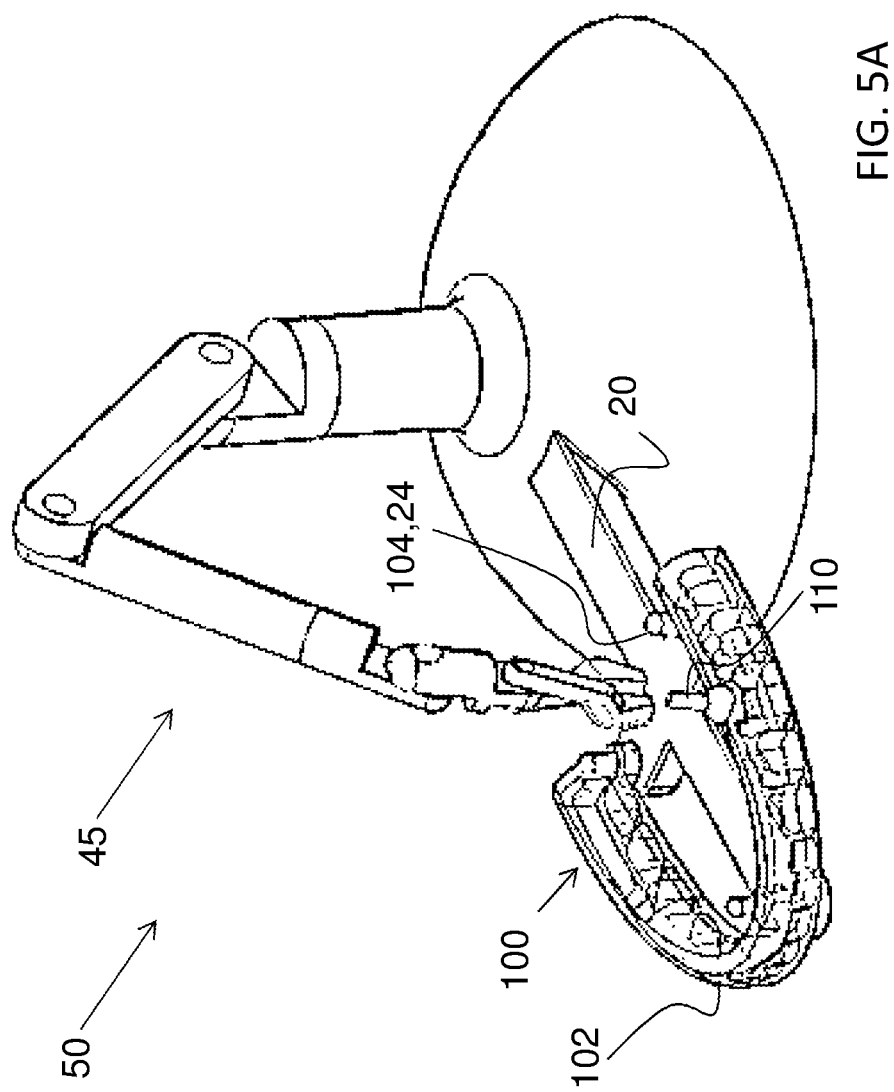

DEVICE, SYSTEM AND METHOD FOR IN-SITU DRILL GUIDE SLEEVE ORIENTATION

RELATED APPLICATIONS

This utility patent application claims priority from U.S. Provisional Application No. 61/693,345 filed on 27 Aug. 2012, the contents of which are fully incorporated herein as if fully set forth.

FIELD OF THE INVENTION

The present invention relates to a device, system and method for producing a dental implant drill guide and in particular to such a device system and method for positioning a sleeve within a drill guide to determine the drill path for positioning a dental implant at an implantation site over an edentulous site.

BACKGROUND OF THE INVENTION

Dental implants are well known in the art and typically include a dental anchor securely inserted into the patient's jawbone, and an abutment member mountable to the dental anchor, the abutment utilized for coupling a restoration.

One of the initial steps in the implantation process and perhaps the most crucial step is determining where to place the implant anchor within the jawbone over the edentulous area. This first initial step is crucial in that it determines the quality of the implantation process and the likelihood of success. Therefore the initial determination of where to drill, at what angle, depth, size, greatly impacts the success of the implantation process. It is extremely important that the hole drilled in the bone tissue has a correct location and inclination with respect to the thickness and morphology of the bone. Care is to be taken to avoid any imperfect fit of the implant, and, most critically, to avoid any perforation or damage to nearby anatomical structures.

In order to facilitate the proper placement, direction, and depth of the drilling process practitioners plan the procedure. In so doing practitioners rely on medical imagery such as X-rays, and computer tomography scans (CT scans) to carefully planned the procedure. The planned procedure generally includes determining the drill sequence, drill location, size and depth. In order to facilitate this process and in order to ensure that the procedure is carried out according to plan, a drill guide has been developed that provides a practitioner with the tool to minimize errors.

A dental drill guide is an acrylic resin mask obtained from a model of the patient's dental arch, adapted to exactly fit over the patient's teeth and/or edentulous areas of the jaw (or just "over the patient's jaw"). The guide mask is provided with one or more guiding holes that are placed in the exact position of the holes to be made or, more preferably, it is provided with one or more metallic hollow cylinders plunged in the resin in the desired location.

Determining the position of the metallic hollow cylinder, also referred to as a stent or a tubular sleeve, is a central and key factor in determining the quality of the drill guide. In planning the implantation procedure, particularly with the aid of modern medical imagery prior to the CAD/CAM production of the drill guide, a clinician can plan the best suited position of the sleeve relative to the medical imagery available.

While this determination is done on the basis of the clinician's knowledge and practice and aided with medical imagery, however, the drill guide itself is generally prepared by a technician and not by the implanting practitioner, therefore lending itself to human error.

More over inherent errors in the medical imagery devices, giving an error of about 10%, leads to further error in determining the location of the sleeve within the drill guide. However such errors are usually not identified until the onset of the implant procedure, itself where a mismatch between the drill guide and the clinical situation before an implanting practitioner is realized.

Most drill guides are limited in that once the template is made its configuration cannot be further adjusted.

Some drill guides provide the option of correcting the sleeve location within the drill guide, as for example the drill guides taught by U.S. Pat. No. 7,905,726 to Stumpel, and Canadian Patent Publication No. 2,484,475 to Csillag. However both Stumpel and Csillag are limited in the range of motion they offer over the edentulous area, specifically they do not provide a full range of motion over the edentulous area. Stumpel and Csillag only provide the opportunity to make incremental changes to the drill guide sleeve rather than allowing a full range and changes to be made to the guide.

SUMMARY OF THE INVENTION

The present invention overcomes the deficiencies of the background by providing a device, system and method for facilitating the determination of a drill path over the entire edentulous area where an implant procedure is to take place. Embodiments of the present invention overcome the deficiencies of the prior art by allowing a practitioner to determine the orientation and position of a drill guide sleeve over the entire edentulous area with a device that provides full range and continuous motion in about both the Buccal-Lingual axis, the Mesio-Distal axis, so as to allow the practitioner to identify the optimal orientation and/or location for the drill path according to the clinical situation at hand.

Preferably the drill guide sleeve orientation device of the present invention provides a practitioner with at least five (5) degrees of freedom in orienting and/or maneuvering a sleeve within the device's housing and over the edentulous area.

Embodiments of the present invention further provide for determining the optimal orientation in-situ in a chair side manner.

Embodiments of the present invention further provide for determining the optimal orientation in-situ in a chair side manner with the option of utilizing medical imagery.

Embodiment of the present invention further allow for corrective measure to be applied, by providing a replaceable orientation device that may be associated and/or disassociated with a guide mold.

Embodiments of the present invention provide for a drill guide sleeve orientation device provided for setting the drill path over an edentulous area, the device including: a housing configured to fit over the entire edentulous area, the housing having a substantially cylindrical body including an outer perimeter surface, an upper surface and a lower surface, wherein the upper and lower surface are provided in the form of a flexible membrane providing maneuverability of a drill guide sleeve along the entire surface of the housing, wherein the housing comprises a substantially open inner lumen, the inner lumen may be filled with a medium that provides for supporting and maneuvering the drill guide sleeve about the housing lumen; and a drill guide sleeve having a distal end, a proximal end, and a medial portion spanning therebetween, wherein the medial portion is disposed within the inner lumen of the housing between the upper surface and the lower surface, and wherein the drill guide sleeve may be maneuvered about the entire surface of the upper surface and the lower surface by manipulating the sleeve at the distal end or the proximal end.

Optionally the medium may be provided in the form of a flowing fluid.

Optionally the medium may be provided in the form of a gel.

Optionally the medium may be provided in the form of a curable gel.

Optionally the medium may be made of biocompatible materials.

Optionally the medium may be provided in the form of an uncured adhesive.

Optionally the medium may be provided in the form of densely packed particles, the particles selected from the group consisting of spheres, microspheres, capsules, gel capsules, glass spheres, beads, silicone bead, or any combination thereof.

Optionally the medium may be a mixture of curable medium and densely packed particles.

Optionally the medium may be provided in the form of a densely packed powder.

Optionally the medium comprises magnetic properties.

Optionally the medium may be a curable medium sensitive to an triggering agent or energy for including but not limited to at least one or more selected from the group comprising: acoustic energy, optical energy, electric filed, magnetic field, electromagnetic field, chemical, wavelength specific electromagnetic filed, temperature change, application of heat, application of cold, the like or any combination thereof.

Optionally the density of the medium may be configured so as to hold and maintain the position of the drill guide sleeve within the housing lumen, prior to curing.

Optionally the housing comprises a fixation and/or curing port. Optionally the curing port may be provided in the form of a unidirectional access port membrane disposed along at least one or more of the housing's surfaces, for example selected from the upper surface, lower surface or perimeter surface, or any combination thereof.

Optionally the flexible member disposed on the upper surface and the lower surface may be configured to be permeable to a curing light.

Optionally the flexible membrane disposed about the upper surface and the lower surface may be provided from curable materials that may be fixed into position when a curing agent may be applied thereto, therein fix the position and orientation of the sleeve.

Optionally the housing may be configured to securely fit within a guide mold along the outer perimeter surface.

Optionally the orientation device's housing may be removed from a guide mold.

Optionally the dimensions of the housing may be configured to fit over an edentulous area corresponding to at least two one or more teeth. Optionally the housing may be malleable and may be customized to fit over any portions of an edentulous area of a jaw.

Optionally the drill guide sleeve may be associated with a dedicated sleeve manipulating tool provided for manipulating the sleeve within the device housing. Optionally a manipulating tool may be linked and/or associated with a computational module.

Optionally the sleeve manipulating tool may further provide for introducing an inner tube member within the lumen of the sleeve.

Optionally the sleeve manipulating tool may further facilitate associating or disassociating the orientation device with the guide mold.

Optionally setting the drill path by depicting the orientation of a guide mold drill guide sleeve over an edentulous area may be performed in-situ in a chair-side manner.

An optional embodiment of the present invention provides a system for orientating a drill guide sleeve within a drill guide mold, the system comprising: a drill guide sleeve orientation device that is associated with a computational module. The computational module provided for facilitating orienting the drill guide sleeve within the orientation device housing while accessing and/or utilizing medical imagery that may be displayed by the computational module.

Optionally the system may further comprise and/or associate with a dedicated sleeve manipulating tool provided to interface between the computational module and the drill guide sleeve orientation device. Optionally and preferably the dedicated tool provides for manipulating the sleeve within the sleeve orientation device housing.

Optionally the dedicated tool may be adapted to provide for manually orienting the sleeve. Optionally the dedicated tool may be an automated robotic device adapted to provide for automated orientation of the sleeve.

Optionally the automated orientation of the sleeve may be provided relative to reference points disposed on the drill guide mold.

Optionally the system may further comprise and/or associate with a computation module stage provided for associating the guide mold with the computational module. Optionally the computational module stage may comprise a plurality of reference point connectors for coupling with corresponding reference point recess disposed about the guide mold.

An optional embodiment of the present invention provides a method for orienting a drill guide sleeve within a guide mold, in situ, in a chair side manner, the method comprising: coupling a drill guide sleeve orientation device, according to embodiments of the present invention, with a guide mold over the edentulous area; placing the guide mold over the dental arch of a patient; associating an orientation tool within the lumen of the sleeve, the orientation tool associated with a computational module comprising a display, displaying a stored medical image of the patient's dental arch, for example a CT scan, and edentulous area; wherein the orientation tool provides a projection of the sleeve onto the stored medical image; while viewing the medical image and the projection of the sleeve, manually maneuvering the sleeve orientation within the housing with the orientation tool over the edentulous area until an optimal orientation of the sleeve is determined; and fixing the position and orientation of the sleeve within the housing by curing the medium.

Optionally the method may further comprise associating an inner tube within the oriented sleeve.

Optionally curing the medium may be provided by introducing a curing agent into the inner lumen of the drill guide sleeve orientation device. Optionally introducing the curing agent may be provided through a dedicated curing port disposed about the housing of the device. Optionally the curing agent may be provided in the form of a curing light.

Unless otherwise defined the various embodiment of the present invention may be provided to an end user in a plurality of formats/platforms, and may be outputted to at least one of a computer readable memory, computer readable media, a computer display device, a printout, a computer on a network or a user.

Unless otherwise defined, all technical and scientific terms used herein have the same meaning as commonly understood by one of ordinary skill in the art to which this invention belongs.

The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

Within the context of this application the term processor, processing module, microprocessor or the like may be used to refer to any device featuring a data processor and/or the like computational properties and/or the ability to execute one or more instructions for example including but not limited to a computer, computer network, PC (personal computer), a server, a minicomputer, a cellular telephone, a smart phone, a PDA (personal data assistant), mobile communication device, mobile processing device, any two or more of such devices in communication with each other, and/or any computer in communication with any other computer, may optionally comprise a "computer network".

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a schematic block diagram of an exemplary drill guide assembly according to optional embodiments of the present invention;

FIG. 2 is a schematic block diagram of an exemplary system according to optional embodiments of the present invention;

FIG. 3A-C are schematic illustrations of an exemplary drill guide sleeve orientation device according to optional embodiments of the present invention;

FIG. 5A-C are a schematic illustration of an exemplary drill guide assembly system according to optional embodiments of the present invention.

DESCRIPTION OF THE PREFERRED EMBODIMENTS

Figure 3A:
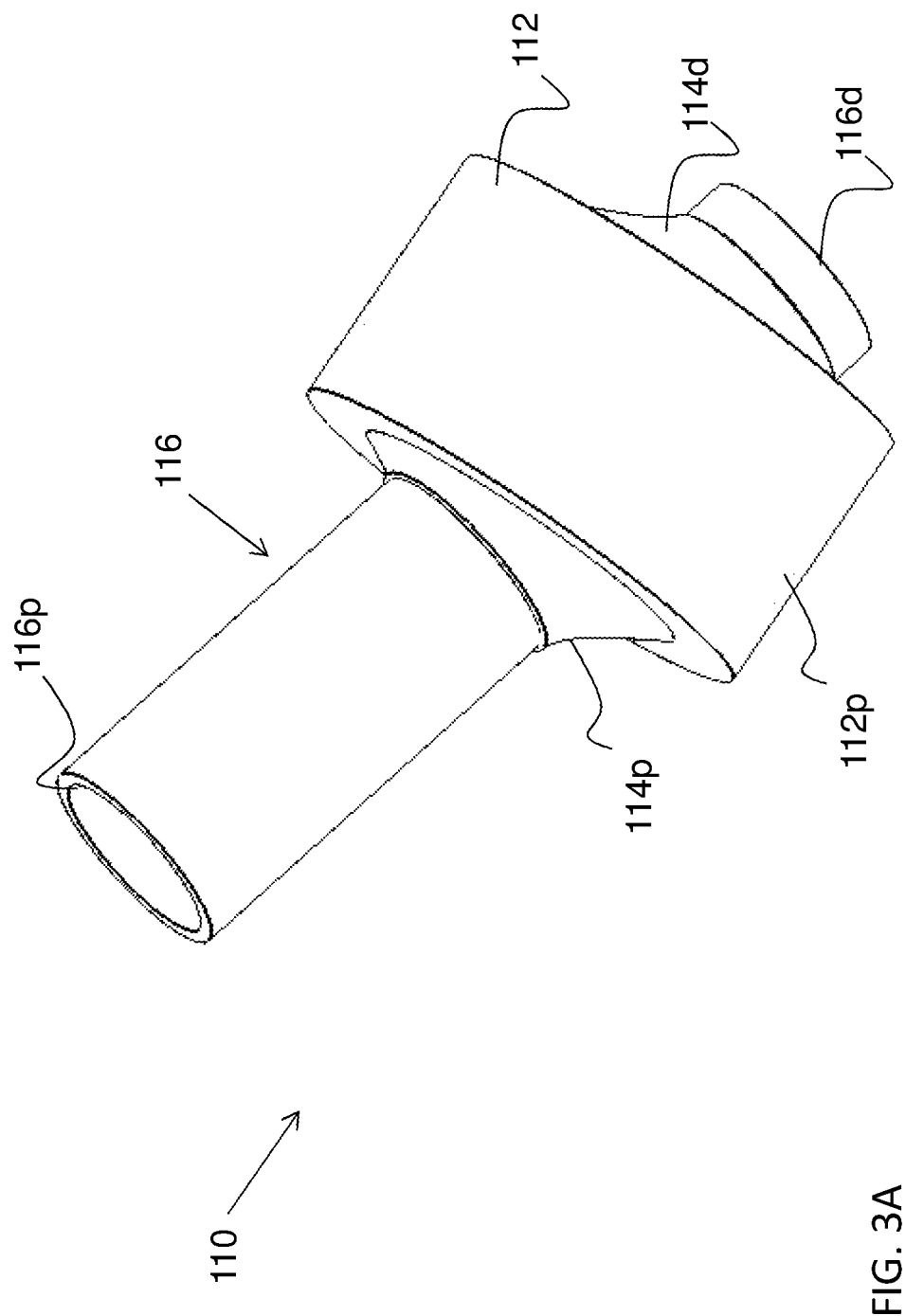

The present invention is of a device, system and method for positioning and orienting a drill guide sleeve within a drill guide to determine the drill path over an edentulous site. Preferably embodiments provide for determining the orientation of the drill guide sleeve in a chair-side manner allowing the implanting clinician to accurately determine the drill path in situ therein taking into account the clinical situation at hand.

The principles and operation of the present invention may be better understood with reference to the drawings and the accompanying description. The following figure reference labels are used throughout the description to refer to similarly functioning components are used throughout the specification hereinbelow.

10 computational module;
12 processor;
14 display;
20 drill guide coupling stage;
24 reference point connectors;
40 dedicated orientation tool;
42 manual orientation tool;
45 automated orientation tool/robotic arm;
50 drill guide system;
100 drill guide;
102 impression mold guide;
104 reference point connectors;
110 sleeve orientation device;
112 housing;
112L housing lumen;
112c curing port;
112m medium;
114 membrane;
114p proximal membrane/upper surface membrane;
114d distal membrane/lower surface membrane;
116 sleeve;
116d sleeve distal end;
116p sleeve proximal end;
116m sleeve medial portion;
116L sleeve lumen;

FIG. 1 shows a schematic illustration of drill guide 100 including an impression guide mold 102 and a sleeve orientation device 110 utilized for orienting stent 116 within guide mold 102.

Preferably impression guide mold 102 includes at a plurality of reference point connectors 104. Optionally and preferably reference point connectors 104 may be utilized as markers which provide for defining a reference coordinate system. Optionally reference point connectors may facilitate the orientation of sleeve 116 with orientation device 110; for example by triangulation.

Optionally connectors 104 may be coupled with or otherwise associated with a proximity location based sensor, for example a RFID tag, optical sensor or the like.

Most preferably drill guide sleeve orientation device 110 provides for setting the drill path over the entire edentulous area where an implantation is to be performed.

Drill guide orientation device 110 comprises housing 112, the membrane 114 and sleeve 116 disposed through housing 112 and membrane 114. Preferably, housing 112 configured to fit over the entire edentulous area, allowing sleeve 116 to be oriented and placed anywhere over the entire edentulous area.

Most preferably housing 112 is configured to allow maximal movement and orientation of sleeve 116 over the entire edentulous area. Most preferably the orientation of sleeve 116 and may be controlled in a fluid and continuous manner in all directions and axis about the edentulous area, including the Buccal-Lingual axis, the Mesio-Distal axis, therein providing a practitioner with at least five degrees of freedom in maneuver sleeve 116. Optionally and preferably sleeve 116 may also provide for determining the depth of the drill path.

Preferably housing 112 is filled with a medium 112m that may be cured allowing sleeve 116 to be fixed in its given orientation within housing 116.

Optionally medium 112m may be provided in the form of a flowing fluid.

Optionally medium 112m may be provided in the form of a gel.

Optionally medium 112m may be provided in the form of a curable gel.

Optionally medium 112m may be provided from biocompatible materials.

Optionally medium 112m may be provided in the form of an uncured adhesive.

Optionally medium 112m may be provided in the form of densely packed particles. Optionally the densely packed particles may for example include but is not limited to spheres, microspheres, capsules, gel capsules, glass spheres, glass micro-spheres, beads, silicone bead, or any combination thereof. Optionally medium 112m may be provided as a mixture of curable medium and densely packed particles.

Optionally medium 112m may be provided in the form of a densely packed powder.

Optionally the density of medium 112m may be configured so as to hold and maintain the position the drill guide sleeve 116 within housing 112.

Optionally medium 112m may be provided as any curable medium that may be fixed upon exposure to a curing agent and/or triggering agent. Optionally triggering agent may for example include but is not limited to a triggering agent and/or energy in the form selected from acoustic energy, optical energy, electric filed, magnetic field, electromagnetic field, chemical, wavelength specific electromagnetic filed, temperature change, application of heat, application of cold, the like or any combination thereof.

Preferably sleeve 116 is provide substantially in the form of an open ended tube having an proximal end 116p, a distal end 116d and a medial portion 116m spanning therebetween.

Optionally sleeve 116 may be maneuvered and/or manipulated within housing 112 manually by a practitioner or with the aid of an optional dedicated tool 40.

Optionally housing 112 may be configured to securely fit within a guide mold 102 along its outer surface 112p. Optionally housing 112 may be configured to be removable from a guide mold 102.

Optionally the dimensions of housing 102 may configured to fit over an edentulous area corresponding to one or more teeth. Optionally housing 102 may be provided from malleable materials and may optionally be customized in its shape and geometry in order to fit over any portions of an edentulous area of a jaw.

FIG. 2 shows a block diagram of a drill guide system 50 that provides for chair-side, in situ determination of a drill path orientation within an edentulous area. System 50 includes drill guide 100, having a sleeve orientation device 110 (as shown in FIG. 1), that may be associated with a computational module 10.

Computation module 10 is preferably provided in the form of a computer or the like device having processing, displaying, memory and communication capabilities. Optionally computer module may be realized as a server, smart phone, PDA or the like. Preferably computational module 10 comprises processing module 12 and display module 14.

Preferably, computation module 10 provides for displaying medical imagery, for example in the form of a CT scan, utilizing display module 14. Optionally processing module 12 may provide for actively processing and updating the displayed medical imagery, relative to changes made to the orientation of sleeve 116.

Optionally computational module 10 may be linked or associated with optional devices for example including a dedicate orientation tool 40, drill guide stage 20, manual orientation tool 42, or automated orientation tool 45.

Optionally computational module 10 may be linked or associated with additional computers and/or servers, as is known in the art. Optionally remote linkage of computation module 10 may optionally allow a practitioner to seek advice and/or input for field experts located remotely, based on the clinical situation being faced.

Drill guide stage 20 provides for associating drill guide 100 with computation module 10, allowing a practitioner to amend and/or correct drill guide 100 while directly linked to computation module 10 allowing the practitioner to visualize a projection of sleeve 116 on a medical imagery displayed via display module 14. Stage 20 provides for chair-side orientation of sleeve 116 when the drill guide is not associated with the patient however enabling a visualization of the patient's oral anatomical structures in relation to sleeve 116, by providing a projection of sleeve 116 on a given medical image.

Stage 20 includes reference point connectors 24 that align and couple with reference point connectors 104 provided on drill guide 100. Preferably the association of reference point connectors 104 and 24 allows computation module 10 to project the orientation of sleeve 116 associated with guide 100 onto medical imagery displayed on display module 14.

Optionally stage 20 may be coupled and/or associated with computation module 10 by wired and/or wireless communication protocols as is known in the art.

Optionally orientation tool 40 may be coupled and/or associated with computation module 10 by wired and/or wireless communication protocols as is known in the art. Optionally an orientation tool 40 may be provided in optional forms including a manual orientation tool 42 or an automated orientation tool 45. Most preferably orientation tool 40 facilitates maneuvering sleeve 116 within housing 112 about the edentulous space.

Most preferably orientation tools 40 may be associated with computation module 10 to enable visualization of the orientation of sleeve 116 relative to medical imagery while sleeve 116 is maneuvered. Therein allowing a practitioner to amend and/or correct drill guide 100 while directly linked to computation module 10 allowing the practitioner to visualize a projection of sleeve 116 onto a medical imagery displayed via display module 14.

Optionally an automated orientation tool 45, for example provided in the form of a robotic arm, for example as shown in FIG. 5A, may be associated with stage 20 while allowing a practitioner to control the orientation of sleeve 116, in a clinical setting. Optionally automated orientation tool 45 may be directly linked to computation module 10 without stage 20.

Optionally the movements of sleeve 116 by orientation tool 45 may be automated or linked to a man machine interface, for example a joystick, via computational module 10. Optionally control of orientation tool 45 may be controlled remotely, for example with a remotely linked computational module 10 for example by a consulting expert.

Figure 5B:
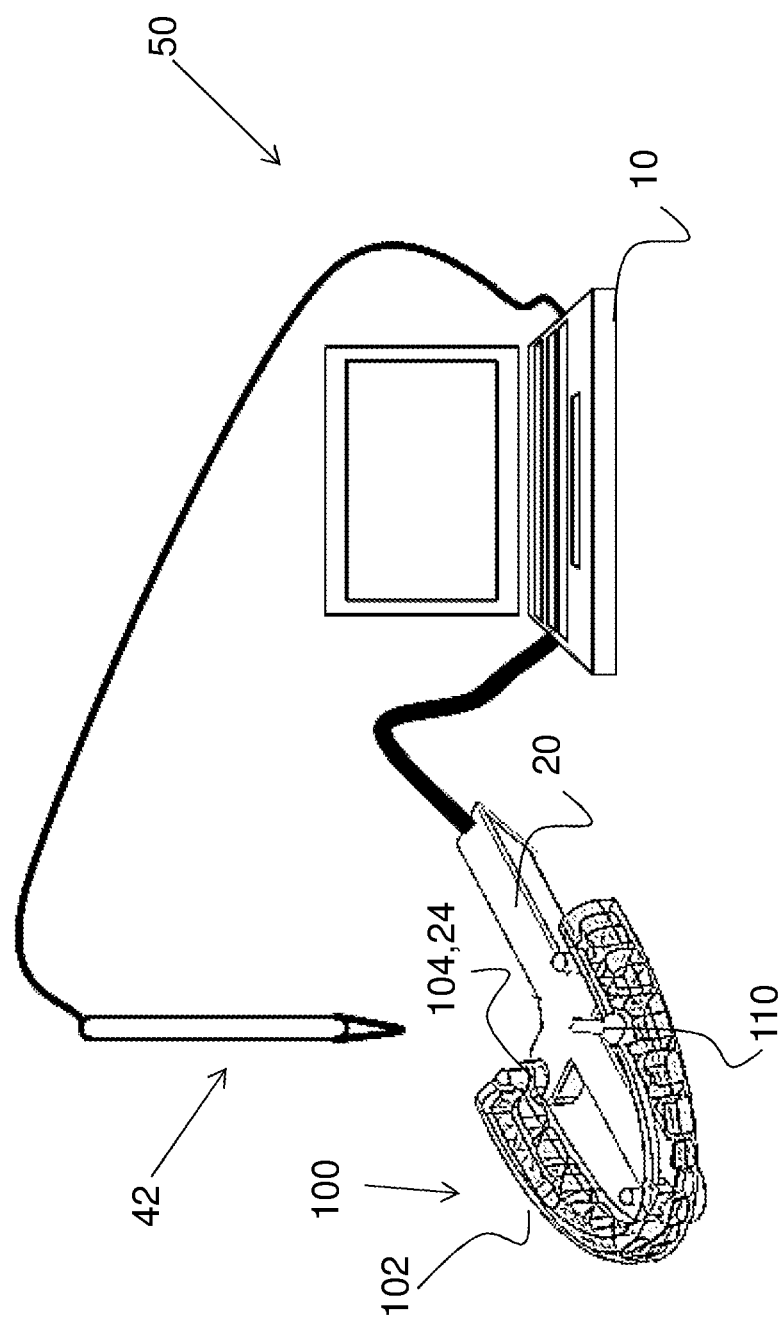

Optionally a manual orientation tool 42, for example as shown in FIG. 5B, may be associated with guide 100 while guide 100 is within the oral cavity of a patient, therein in allowing a practitioner to control the drill path by controlling the orientation of sleeve 116, in situ. Optionally manual orientation tool 42 may be associated with computational module 10 in a wired or wireless manner as is known in the art. Preferably orientation tool 42 may be associated with sleeve 116 through its open lumen allowing tool 42 to control the maneuverability of sleeve 116 within device 110.

FIG. 3A-C show varying perspective view of sleeve orientation device 110 comprising housing 112, sleeve 116 and membranes 114.

Housing 112 is optionally and preferably provided in a substantially cylindrical body including an outer perimeter surface 112p, an upper surface 114p and a lower surface 114d.

Preferably, upper surface 114p and lower surface 114d are provided in the form of a flexible membrane, or the like material, providing maneuverability of a drill guide sleeve 116 along the entire surface of housing 112 preferably defined by perimeter 112p.

Preferably housing 112 comprises a substantially open inner lumen 112L, FIG. 3C, that is filled with a medium 112m that provides for supporting and maneuvering drill guide sleeve 116 within lumen 112L of housing 112.

Preferably, drill guide sleeve 116 has a distal end 116d, a proximal end 116p, and a medial portion 116m, spanning between distal end 116d and the proximal end 116p. Most preferably the medial portion 116m is disposed within inner lumen 112L of housing 112, between upper surface 114p and lower surface 114L.

Preferably drill guide sleeve 116 may be maneuvered about the entire surface of upper surface 114p and lower surface 114d by manipulating or maneuvering sleeve 116 about its distal end 116d or its proximal end 116p.

Figure 4A:
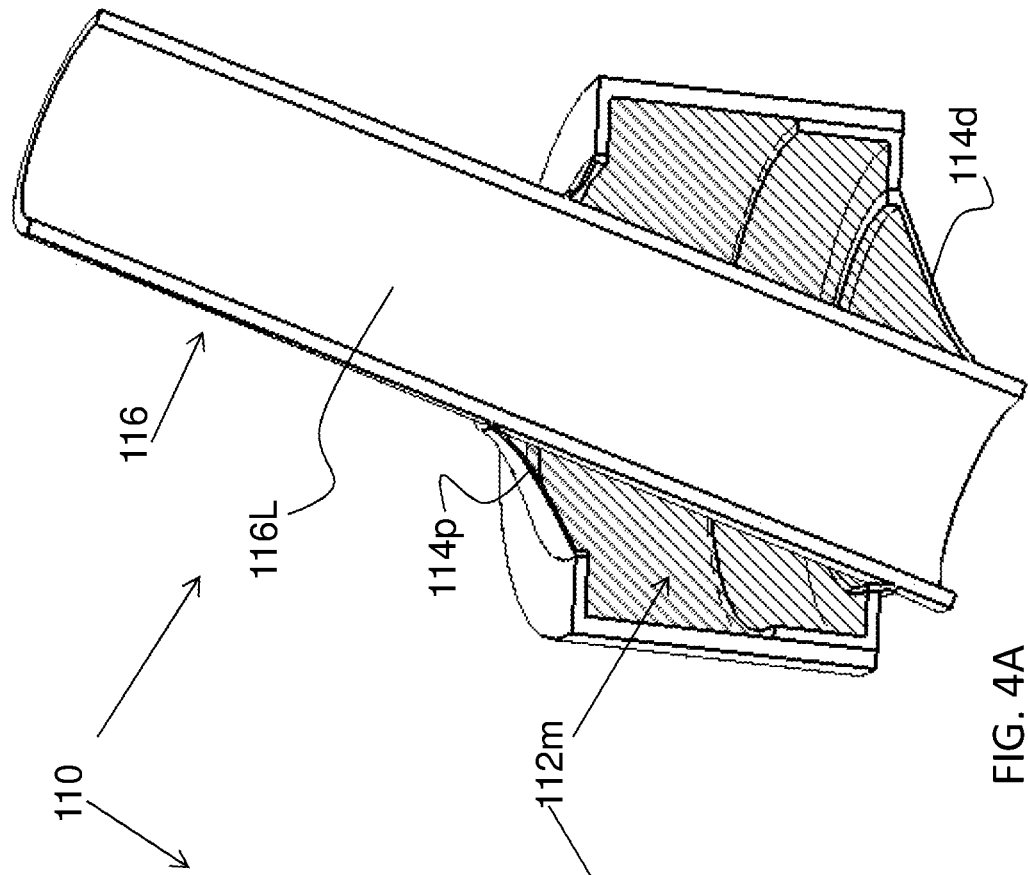
FIG. 4A-B are cross sectional view of schematic illustrations of an exemplary sleeve orientation device according to optional embodiments of the present invention.
Figure 4B:
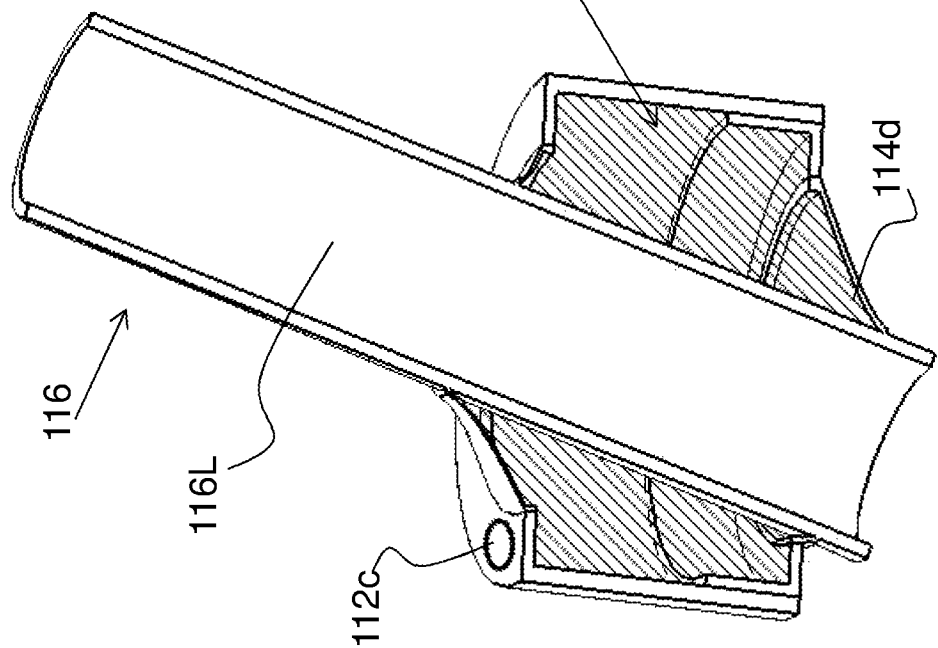

FIG. 4A-B show cross-sectional views of device 110 revealing the inner lumen 112L comprising medium 112m. As previously indicated medium 112m may be provided in optional form. Most preferably medium 112m is a curable medium that provides for fixing sleeve 116 in its place so as to assume the its final orientation within housing 112.

Optionally medium 112m may be cured by various means and/or triggers for example including but not limited to application of an adhesive into lumen 112L, applying and/or introducing a chemical agent and/or reagent to react with the medium, exposing medium 112m to a curing light to a light and/or wavelength sensitive medium, applying a temperature change to a temperature sensitive medium, application of an acoustic energy and/or wavelengths for example in the form of ultrasound, vibration, piezoelectric energy for an acoustically sensitive medium, applying a magnetic field to a corresponding sensitive medium, applying an electrical filed and/or current to a corresponding sensitive medium, the like or any combination thereof.

Optionally and preferably a curing agent may be introduced into lumen 112L via a dedicated curing port 112c, as shown in FIG. 4B. Optionally curing port 112c may be disposed about any portion of housing 112, for example as shown about upper surface 114p.

Optionally curing port 112c may be provided in the form of a unidirectional access port that may be disposed about any portion or surface of housing 112.

Optionally housing 112 and in particular upper surface 114p may be provided as light permeable membrane allowing a curing light to be applied in order to cure medium 112m.

Optionally upper surface 114p and lower surface 114d may be provided from flexible materials that may be fixed into position with the application of a curing agent. In optional embodiment medium 112m may not be cured but rather upper surface 114p and lower surface 114d provided may be cured so as to fix the position and orientation of sleeve 116 within housing 112.

FIG. 5A-B show optional embodiments of system 50 utilizing an orientation tool 40 for maneuvering sleeve 116 within guide 100.

FIG. 5A shows utilizing of an automated orientation tool 45, in the form of a robotic arm. Optionally and preferably robotic arm 45 may be utilized to manipulate sleeve 116 in order to assume the best suited position relative to the clinical situation at hand. Most preferably robotic arm 45 is associated with computation module 10 (not shown) and drill guide 100 via stage 20. Preferably stage 20 is associated with drill guide 100 about at least three reference point connectors 104, 24 disposed thereon.

Optionally stage 20 may be associated with computational module 10 directly or via robotic arm 45. Optionally robotic arm 45 may be used to maneuver sleeve 116 by a clinician in a clinical setting while visualizing the orientation of sleeve 116 relative to medical imagery, as previously described.

FIG. 5B shows an alternative depiction of system 50 similar to that depicted in FIG. 5A, however utilizing a manual orientation tool 42, with stage 20.

Figure 5C:
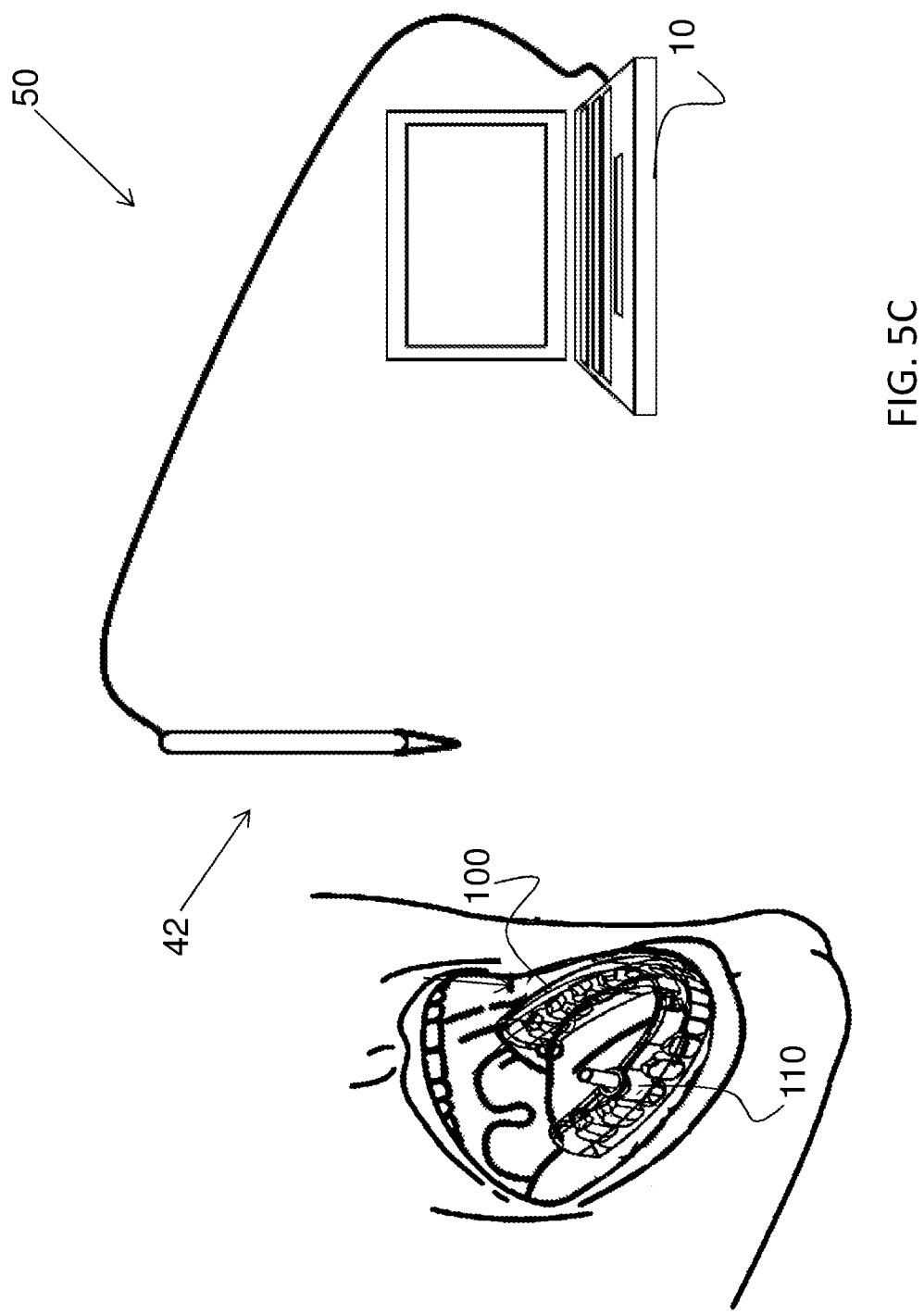

FIG. 5C shows an alternative depiction of system 50, utilizing a manual orientation tool 42, in-situ, as previously described with respect to FIG. 2. Optionally manual orientation tool 42, shown in the form of a sytlet, may be associated with guide 100, while guide 100 is within the oral cavity of a patient, therein in allowing a practitioner to control the drill path by controlling the orientation of sleeve 116, in situ. Optionally and preferably orientation tool 42 may be associated with sleeve 116 through its open lumen 116L allowing tool 42 to control the maneuverability of sleeve 116 within device 110. Optionally manual orientation tool 42 may further associated with computational module 10, in a wired or wireless manner, to allow visualization of sleeve 116 relative to medical imagery, for example in the form of a CT scan, displayed with computational module 10.

Optionally the dedicated sleeve manipulating tool 40, 42, 45 may further provide for introducing an inner tube member concentrically within the sleeve lumen 116L.

Optionally inner tube member may be provided in a tubular structure, similar to that of sleeve 116 having an open lumen provided for receiving a drill bit. Optionally inner tube may be readily associated within sleeve lumen 116L.

Optionally tool 42 may be configured to provide for associating and/or introduce device 110 within a guide mold 102. Optionally tool 42 may be configured to provide for removing and/or disassociating and/or releasing device 110 from guide mold 102. For example if a mistake was make in the orientation of sleeve 116 an erroneous sleeve orientation device 110 may be wholly removed from mold 102 and replace with a new one so as to allow for re-determination, correction and re-orientation of a new sleeve member 116 within the oral cavity, optionally such removal and introduction may be facilitated with a dedicated manipulating tool 42.

Figure 6:
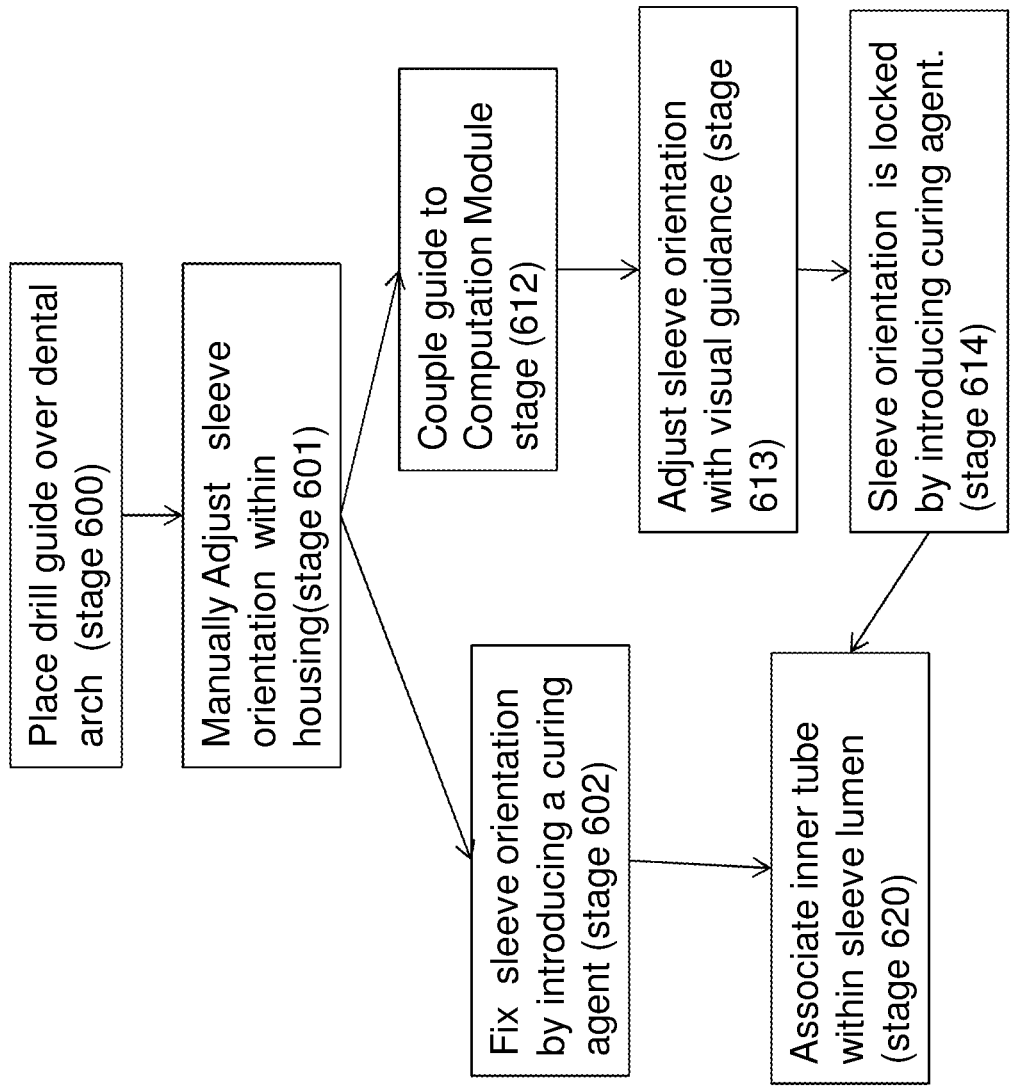
FIG. 6 is a flowchart of an exemplary method according to optional embodiments of the present invention.

FIG. 6 shows a flowchart of a method utilizing sleeve orientation device 110 in a chair-side manner in a clinical setting. In stage 600, a prefabricated drill guide 100 comprising orientation device 110 is associated with a patient's dental arch over an edentulous area. Most preferably the orientation and drill path of sleeve 116 has not yet been fixed within housing 112 of device 110. Next in stage 601, both the location and orientation of sleeve 116 is adjusted by a clinician to assume the clinically optimal orientation over the entire edentulous site so as to ensuring optimal results for the overall implant procedure. Optionally stage 601 may be performed with the assistance of an orientation tool 42 as previously described, with or without medical imagery visualization.

Next in stage 602 a clinician may fix the location and orientation and sleeve 116 over the edentulous area by introducing and/or applying a curing agent as previously described.

Optionally before sleeve 116 is fixed within housing 112 a clinician may choose to validate the selected location and orientation of sleeve 116 with reference to available medical imagery. This may optionally be accomplished within the oral cavity with the aid of a manual orientation tool 42 associated with a computational module as previously described. Optionally, in stage 612, the orientation of sleeve 116 may be validated utilizing a stage 20 in conjunction with an automated orienting tool 40,45, as previously described. In stage 612, guide 100 is associated with stage 20 and computational module 10 to visualize sleeve 116 relative to the available medical imagery on display 14. Next, in stage 613 the location and orientation of sleeve 116 is adjusted as needed relative to the medical imagery. Next in stage 614 sleeve 116 is fixed within housing 112 by introducing or exposing device 110 with an optional curing agent as previously described.

Next in stage 620 an inner tube is introduced within sleeve lumen 116L, optionally with the aid of tools 40,42, allowing a clinician to initiate the procedure.

While the invention has been described with respect to a limited number of embodiment, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not described to limit the invention to the exact construction and operation shown and described and accordingly, all suitable modifications and equivalents may be resorted to, falling within the scope of the invention.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention defined by the appended claims.

Further modifications of the invention will also occur to persons skilled in the art and all such are deemed to fall within the spirit and scope of the invention as defined by the appended claims.

While the invention has been described with respect to a limited number of embodiments, it will be appreciated that many variations, modifications and other applications of the invention may be made.

What is claimed is:

1. A drill guide sleeve orientation device for setting the drill path over an edentulous area, the device including:
   a) a housing configured to fit over the entire edentulous area, said housing having a substantially cylindrical body including an outer perimeter surface, an upper surface and a lower surface, wherein said upper and lower surface are provided in the form of a flexible membrane providing maneuverability of a drill guide sleeve along the entire surface of said housing, wherein said housing comprises a substantially open inner lumen, said inner lumen is filled with a medium that provides for supporting and maneuvering said drill guide sleeve about said housing; and
   b) a drill guide sleeve having a distal end, a proximal end, and a medial portion spanning between said distal end and said proximal end, wherein said medial portion is disposed within said inner lumen of said housing between said upper surface and said lower surface, and wherein said drill guide sleeve configured to be maneuvered about the entire surface of said upper surface and said lower surface by manipulating said sleeve about said distal end or said proximal end.

2. The device of claim 1 wherein said medium is provided in the form of a flowing fluid.

3. The device of claim 1 wherein said medium is provided in the form of a gel.

4. The device of claim 1 wherein said medium is provided in the form of a curable gel.

5. The device of claim 1 wherein said medium is made of biocompatible materials.

6. The device of claim 1 wherein said medium is provided in the form of an uncured adhesive.

7. The device of claim 1 wherein said medium is provided in the form of densely packed particles, said particles selected from the group consisting of spheres, microspheres, capsules, gel capsules, glass spheres, beads, silicone bead, or any combination thereof.

8. The device of claim 1 wherein said medium is a mixture of curable medium and densely packed particles.

9. The device of claim 1 wherein said medium is provided in the form of a densely packed powder.

10. The device of claim 1 wherein said medium comprises magnetic properties.

11. The device of claim 1 wherein said medium is a curable medium sensitive to an triggering agent or energy selected form the group consisting of: acoustic energy, optical energy, electric filed, magnetic field, electromagnetic field, chemical, wavelength specific electromagnetic filed, temperature change, application of heat, application of cold or any combination thereof.

12. The device of claim 1 wherein the density of said medium is configured so as to hold and maintain the position of said drill guide sleeve within said housing lumen.

13. The device of claim 1 wherein said housing comprises a curing port.

14. The device of claim 1 wherein said curing port is provided in the form of a unidirectional access port membrane disposed on one of said upper surface, lower surface or perimeter surface.

15. The device of claim 1 wherein said flexible member disposed on said upper surface and said lower surface is permeable to a curing light.

16. The device of claim 1 wherein said flexible membrane disposed about said upper surface and said lower surface provided from curable materials that fixed into position when a curing agent is applied thereto, therein fixing the position and orientation of said sleeve.

17. The device of claim 1 wherein said housing is configured to securely fit within a guide mold along said outer perimeter surface.

18. The device of claim 1 wherein said housing is configured to be removed from a guide mold.

19. The device of claim 1 wherein the dimensions of said housing is configured to fit over an edentulous area corresponding to one or more teeth.

20. The device of claim 1 wherein said housing is malleable and configured to be customized to fit over any portions of an edentulous area of a jaw.

21. The device of claim 1 wherein said drill guide sleeve is configured to be associated with a dedicated sleeve manipulating tool provided for manipulating said sleeve within said device housing.

22. The device of claim 21 wherein said manipulating tool is configured to be linked and/or associated with a computational module.

23. The device of claim 21 wherein said sleeve manipulating tool further provides for introducing an inner tube member within the lumen of said sleeve.

24. The device of claim 21 wherein said sleeve manipulating tool further facilitates associating or disassociating said device with said guide mold.

25. The device of claim 1 wherein setting the drill path over an edentulous area is performed in-situ in a chair-side manner.

26. A system for orientating a drill guide sleeve within a drill guide mold, the system comprising: the drill guide sleeve orientation device according to claim 1 that is associated with a computational module provided for facilitating orienting said drill guide sleeve within said housing while utilizing medical imagery displayed by said computational module.

27. The system of claim 26 further comprising a dedicated sleeve manipulating tool provided to interface between said computational module and said drill guide sleeve orientation device and wherein said dedicated tool provides for manipulating said sleeve within said device housing.

28. The system of claim 27 wherein said dedicated tool is adapted to provide for manually orienting said sleeve.

29. The system of claim 27 wherein said dedicated tool is an automated robotic device adapted to provide for automated orientation of said sleeve.

30. The system of claim 27 wherein said automated orientation of said sleeve is provided relative to reference points disposed about said guide mold.

31. The system of claim 26 further comprising a computation module stage for associating said guide mold with said computational module.

32. The system of claim 31 wherein said stage comprises a plurality of reference point connectors for coupling with corresponding reference point recess disposed about said guide mold.

33. A method for orienting a drill guide sleeve within a guide mold, in situ, the method comprising:
  a) coupling a drill guide sleeve orientation device according to claim 1 with a guide mold over said edentulous area;
  b) placing said guide mold over the dental arch of a patient;
  c) associating an orientation tool within the lumen of said sleeve, said orientation tool associated with a computational module comprising a display, displaying a stored medical image of the patient's dental arch and edentulous area; wherein said orientation tool provides a projection of said sleeve on said stored medical image;
  d) while viewing said medical image and the projection of said sleeve, manually maneuvering said sleeve within said housing with said orientation tool over said edentulous area until an optimal orientation of said sleeve is determined; and
  e) fixing the position and orientation of said sleeve within said housing by curing said medium.

34. The method of claim 33 wherein curing said medium is provided by introducing a curing agent into the inner lumen of said drill guide sleeve orientation device.

35. The method of claim 34 wherein introducing said curing agent is provided through a dedicated curing port disposed about the housing of said device.

36. The method of claim 34 wherein said curing agent is provided in the form of a curing light.

37. The method of claim 33 further comprising: f) associating an inner tube within said sleeve.

* * * * *